United States Patent [19]
Kamber et al.

[11] B 3,994,871
[45] Nov. 30, 1976

[54] PROCESS FOR THE MANUFACTURE OF PEPTIDES CONTAINING CYSTINE

[75] Inventors: Bruno Kamber, Basel; Peter Sieber, Reinach; Bernhard Riniker, Frenkendorf, all of Switzerland; Albert Hartmann, Grenzach, Germany; Werner Rittel, Basel, Switzerland

[73] Assignee: Ciba-Geigy Corporation, Ardsley, N.Y.

[22] Filed: May 20, 1974

[21] Appl. No.: 471,617

[44] Published under the second Trial Voluntary Protest Program on February 10, 1976 as document No. B 471,617.

[30] Foreign Application Priority Data

May 24, 1973 Switzerland.......................... 7526/73
Sept. 14, 1973 Switzerland...................... 13274/73

[52] U.S. Cl..................... 260/112.5 R; 260/112.7
[51] Int. Cl.$^2$................ C07C 103/52; A61K 37/26; C07G 7/00
[58] Field of Search...................... 260/112.5, 112.7

[56] References Cited
OTHER PUBLICATIONS
Hermann et al.: Chem. Abstr. 78: 136,656m, (1973).
Kamber: Chem. Abstr. 78: 124,894z, (1973).
Moroder et al.: Chem. Abstr. 78: 160,089z, (1973).

*Primary Examiner*—Lewis Gotts
*Assistant Examiner*—Reginald J. Suyat
*Attorney, Agent, or Firm*—Joseph G. Kolodny; John J. Maitner; Theodore O. Groeger

[57] ABSTRACT

Process for the manufacture of peptides which contain more than one disulphide bond characterized in that in one or two aminoacid sequences containing cysteine, in which disulphide bonds are to be produced, two cysteine radicals which are to be linked are protected by a mercapto-protective group $R_1$ of the aralkyl type, two further cysteine radicals are protected by an acylaminomethyl group $R_2$, the protective groups $R_1$ are removed by treatment with iodine in the presence of a polyhalogenated lower aliphatic hydroxy compound or oxo compound, or a corresponding lower alkanoic acid lower alkyl ester, at the same time forming the disulphide bond between these cysteine radicals, which are protected by $R_1$, and at any desired point after removal of the polyhalogenated compound the second disulphide bridge is formed in the usual manner.

15 Claims, No Drawings

PROCESS FOR THE MANUFACTURE OF PEPTIDES CONTAINING CYSTINE

The subject of the invention is a new process for the manufacture of peptides which contain more than one cystine-disulphide bond. Such peptides are, for example, insulins, proinsulins, growth hormones, ribonuclease, lysozyme, apamine, relaxins, somatomedins, nerve growth factor (NGF) or epidermal tissue growth factor (EGF) and fragments or synthetic analogues of these natural substances or derivatives thereof, for example, in the case of insulin, compounds consisting of an A- and B-chain, which are linked to one another by peptide chains or by non-peptide bridges, compare Biochem. Biophys. Res. Comm. 55, 60 (1973).

In the synthetic manufacture of such peptides, the problem arises of oxidising the cysteine-containing aminoacid sequences in such a way that the disulphide bonds are formed between the desired cysteine radicals, which can be present in one chain or in two chains.

It has hitherto not been possible to solve the problem satisfactorily by the use of the known selectively removable mercapto-protective groups. Groups which can be removed by alkaline reagents or hydrogenolytically are not advantageous, if only because under the conditions of their removal a partial decomposition of the peptide, especially at the disulphide bond, occurs. In the case of the protective groups which can be split off under acid conditions, adequate selectively is difficult to attain. A further great difficulty is that when the mercapto groups required for the first disulphide bond have been liberated by means of selectively removable mercapto-protective groups and the disulphide bond has been formed therefrom by oxidation, a further mercapto group, which is still protected by a different protective group, can, after removal of the protective group, react with the disulphide bond, with disproportionation of the molecule.

A process has now been found by which peptides or peptide derivatives with more than one disulphide bond can be manufactured in a surprisingly advantageous manner.

The process is based on the selective removability of mercapto-protective groups in polyhalogenated lower aliphatic hydroxy or oxo compounds, above all lower alkanols, especially trifluoroethanol or hexafluoro-2-propanol.

Known mercapto-protective groups for cysteine radicals are those of the aralkyl type, for example trityl, and acylaminomethyl groups, for example acetylaminomethyl. These groups can advantageously be split off by means of iodine, with oxidation to the cystine radical occurring simultaneously, compare British Pat. Nos. 1,259,017 and 1,329,860. It has been found that these two types of mercapto-protective groups can very effectively be removed selectively if the cysteine-peptide containing the two types of protective groups are treated with iodine in the polyhalogenated compounds mentioned, especially trifluoroethanol or 1,1,1,3,3,3-hexafluoro-2-propanol. In the course thereof, only the two aralkyl-protected cysteine radicals are oxidised to cystine, whilst the acylaminomethyl protective group remains preserved unchanged. Thus, a peptide derivative with a cystine-S-S bridge in the desired position, and still containing one or two acylaminomethyl-protected cysteine radicals, is obtained. The second disulphide bond can, after removal of the polyhalogenated compound, also be produced by treatment with iodine. However, it is also possible to use other oxidising agents for forming the disulphide bridge from the acylaminomethyl-protected mercapto groups, for example phenyl iodosoacetate or bromates such as potassium bromate. The acylaminomethyl-protected mercapto groups can also be oxidised to the disulphide electrochemically, for example at a gold, platinum or carbon anode. Furthermore, the acylaminomethyl group can be split off by the action of heavy metal ions, for example mercury-(II) ions or silver ions, and the mercaptides thereby obtained can be converted to the disulphide compound by oxidation, for example with iodine, potassium ferricyanate or other oxidising agents. The formation of the second disulphide bridge does not have to be carried out immediately following the formation of the first disulphide bridge (from the aralkyl-protected mercapto groups), and can instead be carried out at any desired point during the peptide synthesis, for example after lengthening one or both aminoacid chains.

The process according to the invention is accordingly characterised in that in one or two aminoacid sequences containing cysteine, in which disulphide bonds are to be produced, two cysteine radicals which are to be linked are protected by a mercapto-protective group $R_1$ of the aralkyl type, two further cysteine radicals are protected by an acylaminomethyl group $R_2$, the protective groups $R_1$ are removed by treatment with iodine in the presence of a polyhalogenated lower aliphatic hydroxy compound or oxo compound, at the same time forming the disulphide bond between these cysteine radicals, which were protected by $R_1$, and at any desired point after removal of the polyhalogenated compound the second disulphide bridge is formed.

The process has the advantage that good selective oxidation of the cysteine groups is achieved in a simple manner. The selectivity manifests itself in the fact that, for example, S-trityl-protected cysteine radicals are practically instantaneously converted, in 100% yield, into cystine by means of iodine at room temperature in the presence of trifluoroethanol or hexafluoro-2-propanol, whilst under these conditions acetylaminomethyl-protected cysteine radicals remain entirely unchanged.

By mercapto-protective groups $R_1$ of the aralkyl type there are to be understood groups in which the carbon atom carrying at least one aryl radical is bonded to the sulphur of the mercapto group. An aryl radical can be monocyclic or bicyclic (for example naphthyl); above all, it is a phenyl radical which is unsubstituted or is substituted by electron-donor substituents, for example by one or more radicals from the group of lower alkyl, lower alkoxy and halogen. The aliphatic part of the aralkyl radical is a lower alkyl or cycloalkyl radical with up to 7 carbon atoms, especially methyl. In addition to the aryl radical, $R_1$ contains at least one further cyclic radical which is either an aryl radical, such as indicated, or a cycloalkyl radical with 5–7 carbon atoms. As examples of the radicals $R_1$ there may be mentioned 1-phenylcyclopentyl, 1-phenylcyclohexyl, 1-phenylcycloheptyl, p-methoxyphenylcyclohexyl, 1,1-diphenylethyl and di-(p-tolyl)-ethyl, but especially triphenylmethyl (Trt).

By an acylaminomethyl group $R_2$ there is to be understood a group of the formula $-CH_2-NH-CO-R$ wherein CO—R denotes the acyl radical of a carboxylic acid, such as of an aliphatic, aromatic, araliphatic or heterocyclic carboxylic acid or of a carbonic acid derivative, such as a carbonic acid ester radical or carbamic acid radical. Above all, R is an optionally substituted lower alkyl radical, for example a methyl, ethyl, propyl, isopropyl, n-butyl or tert.-butyl radical which can, for example, contain, as substituents, halogen atoms such as fluorine, chlorine, bromine or iodine, trifluoromethyl or the nitro group. Further, R is, for example, an optionally substituted cycloalkyl radical with 3–8, preferably 5–6, ring atoms, such as the cyclopentyl or cyclohexyl radical, or an optionally substituted aromatic or araliphatic radical, wherein the aromatic ring is preferably the benzene ring, above all optionally substituted phenyl or benzyl, for example phenyl or benzyl which are unsubstituted or substituted in the phenyl radical by lower alkyl, lower alkoxy, halogen or nitro, or a heterocyclyl radical, above all a monocyclic heterocyclyl radical, which is optionally substituted as mentioned, for example the thienyl or furyl radical. Preferably, $R_2$ represents the acetylaminomethyl group (Acm).

The treatment with iodine in order to split off the mercapto-protective group $R_1$, with simultaneous oxidation of the cysteine groups to the cystine group is carried out, according to the invention, in the presence of a polyhalogenated lower hydroxy or oxo compound, as already mentioned, possible halogen atoms being bromine, chlorine and especially fluorine. The reaction medium should preferably contain at least 40% by weight of the polyhalogenated compound. In addition, the reaction medium can contain water or aqueous or organic solvents or mixtures of solvents, especially iodine solvents or water. If water is present in the mixture, its proportion by weight is preferably 0–30%.

Polyhalogenated lower aliphatic hydroxy or oxo compounds are above all polyhalogenated lower alkanols and di-lower alkyl ketones with 2 to 5, especially 2 to 3, carbon atoms, and also corresponding lower alkanoic acid lower alkyl esters, for example polyhalogenated acetic acid lower alkyl esters such as trifluoroacetic acid methyl ester or trichloroacetic acid ethyl ester. The compounds are preferably perhalogenated, at least on an otherwise unsubstituted carbon atom. Preferred examples are 2,2,2-tribromoethanol, 2,2,2-trichloroethanol, 1,1,1-trifluoroacetone, hexachloroacetone, hexafluoroacetone and especially 2,2,2-trifluoroethanol and 1,1,1,3,3,3-hexafluoro-2-propanol. As iodine solvents there should above all be mentioned halogenated hydrocarbons, especially chlorinated lower alkanes such as methylene chloride, chloroform, carbon tetrachloride and tetrachloroethane and also, for example, lower alkanols such as methanol, ethanol, propanol, glacial acetic acid, ethyl acetate, dioxane, acetonitrile, dimethylformamide, dimethylsulphoxide and aqueous potassium iodide solution.

At times, a content of water or aqueous acetic acid in the reaction medium can be of advantage.

The reaction with iodine is carried out under reaction conditions which are in themselves known, for example as described in British Pat. No. 1,259,017. Preferably, the reaction is carried out at room temperature, but it is also possible to use lower or higher temperatures, for example from 0° to 100°, depending on the nature of the peptide.

The reaction takes place at an acid pH, which is created through the hydrogen iodide formed during the reaction. If desired, the pH can be adjusted to 4–5 by means of buffers. If the reaction is carried out at a pH above 4, side chain hydroxyl groups of tyrosine which may be present in the peptide sequence should be protected, for example by the tert.-butyl ether group, to prevent an iodination.

Preferably, an excess of iodine is used. The iodine can be mixed in a solid or dissolved form with the peptide solution. The excess iodine can be removed from the resulting solution by, for example, extraction or, for example, with thiosulphate or ascorbic acid; alternatively, the peptide can be precipitated from the solution, and separated off.

The removal of the $R_2$ protective group with simultaneous formation of the second disulphide bridge can, if desired, also be carried out with iodine, as described in British Pat. No. 1,329,860. Aqueous, aqueous-organic or organic solvents, with the exception of polyhalogenated lower alkanols, can be used, and pure or aqueous acetic acid is used with advantage.

In the process according to the invention, the amino groups in the aminoacid sequences used as starting materials can be present in a protonised form or be protected by customary amino-protective groups. Hydroxyl and carboxyl groups can also, if desired, be present in a protected form. Strongly acid-labile amino-protective groups such as trityl are split off under the reaction conditions.

As examples of amino-protective groups there should be mentioned: acyl groups such as formyl, trifluoroacetyl, phthaloyl, p-toluenesulphonyl, benzylsulphonyl, benzenesulphenyl and o-nitrophenylsulphenyl or, above all, groups derived from carbonic acid or thiocarbonic acid, such as carbobenzoxy groups which are optionally substituted in the aromatic radical by halogen atoms, nitro groups, lower alkyl or lower alkoxy or lower carbalkoxy groups, for example carbobenzoxy, o-bromo-, p-bromo- or p-chloro-carbobenzoxy, 2,4-dichlorocarbobenzoxy, p-nitrocarbobenzoxy and p-methoxycarbobenzoxy, coloured benzyloxycarbonyl groups such as p-phenylazo-benzyloxycarbonyl and p-(p'-methoxyphenylazo)-benzyloxycarbonyl, tolyloxycarbonyl, ($\alpha,\alpha$-dimethyl-3,5-dimethoxybenzyl)-oxycarbonyl, benzhydryloxycarbonyl, 2-phenyl-isopropoxycarbonyl, 2-tolylisopropoxycarbonyl and above all 2-(para-biphenylyl)-2-propoxycarbonyl, as well as aliphatic oxycarbonyl groups such as, for example, 1-methylcyclobutoxycarbonyl, isonicotinyloxycarbonyl, allyloxycarbonyl, cyclopentyloxycarbonyl, tert.-amyloxycarbonyl, adamantyloxycarbonyl, isobornyloxycarbonyl and above all tert.-butoxycarbonyl.

Carboxyl groups can be protected, for example by amide or hydrazide formation or by esterification. Suitable compounds for the esterification are, for example, lower optionally substituted alkanols such as methanol, ethanol, cyanomethyl alcohol, benzoylmethyl alcohol or especially tert.-butanol, and also aralkanols such as aryl-lower alkanols, for example benzyl or benzhydryl alcohols which are optionally substituted by lower alkyl or lower alkoxy groups or halogen atoms, such as p-nitrobenzyl alcohol or 2,4,6-trimethylbenzyl alcohol, or phenols and thiophenols, such as phenol, thiophenol and thiocresol.

The hydroxyl groups of the serine, threonine and tyrosine radicals can be protected, for example by esterification or etherification. Suitable acyl radicals for the esterification are, for example, lower alkanoyl radicals such as acetyl, aroyl radicals such as benzoyl and above all radicals derived from carbonic acid, such as benzyloxycarbonyl, o-bromobenzyloxycarbonyl or ethoxycarbonyl. Suitable groups for the etherification are, for example, benzyl, m-bromobenzyl, 2,6-dichlorobenzyl, tetrahydropyranyl or tert.-butyl radicals. The hydroxyl groups can also be protected by the 2,2,2-trifluoro-1-tert.-butoxycarbonylaminoethyl or -1-benzyloxycarbonylaminoethyl groups (Weygand) described in Ber. 100 (1967), 3838–3849.

Above all, protective groups which can be split off acidolytically, for example by acetic acid, trifluoroacetic acid, hydrochloric acid or hydrogen fluoride, are used, especially groups of the tert.-butyl type, such as the tert.-butoxycarbonyl group, the tert.-buty ester group and the tert.-butyl ether group. Here it is necessary to take account of the fact that when synthesising the sequences by chain lengthening at the amino end, the various chains must carry amino-protective groups which can be split off selectively relative to one another, as described in German Offenlegungsschrift 2,346,147 or Belgian Pat. No. 805,147 (Case 4-8148). As explained there, so-called stable protective groups are required as groups to be retained constantly, for example for the protection of amino, hydroxyl and carboxyl groups of the side chains and for the protection of terminal carboxyl groups, and in addition, two types of so-called labile protective groups are required for the α-amino groups of the different chains undergoing synthesis. The process is illustrated in German Offenlegungsschrift 2,346,147 for a partial sequence of human insulin, namely A-chain 14–21 + B-chain 17–30, which is also used in the process, described in the present application, for the manufacture of human insulin. Here, the 2-(p-biphenylyl)-2-isopropoxycarbonyl group and the trityl group are used as amino-protective groups for the two chains. The content of the said German Offenlegungsschrift and of Belgian Pat. No. 805,147 should be consulted to supplement the present application.

If the present process gives protected peptides containing cystine, these can be used direct for the synthesis of peptides with a longer aminoacid chain or, if desired, the protective groups can be removed in a known manner.

The starting materials for the process of the present application, namely aminoacid sequences containing cysteine, in which the cysteine radicals are protected by mercapto-protective groups $R_1$ or $R_2$, are known or can be manufactured according to methods which are in themselves known, compare, for example, British Pat. Nos. 1,259,017 (Case 4-6461) and 1,329,860 (Case 4-6914), which also describe the removal of these protective groups. The aminoacid sequences containing cysteine can also contain one or more cystine-S-S bridges which were formed at an earlier point of the synthesis, in the same manner or in a different manner.

The starting materials containing cysteine, and the end products, for example insulin, to be manufactured by means of sequences containing cystine, are obtained by condensing the aminoacids required for the synthesis of the peptide with one another in any desired time sequence, with formation of CONH bonds, with functional groups not participating in the reaction being temporarily protected and the cysteine radicals being oxidised to cystine radicals at any desired point in time.

The protective groups to be used have already been mentioned.

The linkage of the aminoacid units and/or peptide units is carried out, for example, by reacting an aminoacid or a peptide having a protected α-amino group and an activated terminal carboxyl group with an aminoacid or a peptide having a free α-amino group and a free or protected, for example, esterified or amidised, terminal carboxyl group, or reacting an aminoacid or a peptide, having an activated α-amino group and a protected terminal carboxyl group, with an aminoacid or a peptide having a free terminal carboxyl group and a protected α-amino group. The carboxyl group can, for example, be activated by conversion to an acid azide, acid anhydride, acid imidazolide, acid isoxazolide or an activated ester, such as a cyanomethyl ester, carboxymethyl ester, p-nitrophenyl thioester or p-nitrophenyl ester, 2,4,5-trichlorophenyl ester, pentachlorophenyl ester, N-hydroxysuccinimide ester, N-hydroxyphthalidimide ester, 8-hydroxyquinoline ester or N-hydroxypiperidine ester, or by reaction using a carbodiimide (optionally with the addition of N-hydroxysuccinimide or an unsubstituted or, for example, halogen-, methyl- or methoxy-substituted 1-hydroxybenzotriazole) or N,N'-carbonyldiimidazole, and the amino group can be activated, for example, by reaction with a phosphite-amide. The most customary methods to be mentioned are the carbodiimide method, the azide method, the activated ester method and the anhydride method and also the Merrifield method and the N-carboxyanhydride or N-thiocarboxyanhydride method.

The process according to the invention can be used for the synthesis of any desired peptides, or peptide derivatives, containing cystine. By derivatives there are in particular to be understood peptide-amides, and also peptides or peptide-amides in which functional groups such as, for example, amino groups, carboxyl groups or hydroxyl groups, are protected in a known manner, as well as compounds which instead of one or more of the cystine halves contain β-mercaptopropionic acid radicals (desaminocysteine).

According to the process of the invention, peptides containing cystine are to be understood to mean both peptides which contain several cystine radicals in the same chain, and, above all, those in which one or more disulphide bridges link different aminoacid sequences, such as is the case, for example, with insulin with regard to the cystine radical of the A-chain (7-position) and of the B-chain (7-position) and of the A-chain (20-position) and the B-chain (19-position). An example of the presence of a disulphide bridge in one and the same chain and of a second disulphide bridge between two different chains would be the cystine group of positions 6 and 11 of the A-chain of insulin and the cystine group of position 7 of the A-chain and of position 7 of the B-chain.

The invention also relates to a new process for the manufacture of insulin, which utilises the combination of mercapto-protective groups which has been mentioned and their removal in a polyhalogenated hydroxy or oxo compound. This process is characterised in that a sequence is prepared which contains at least the aminoacids 6–11 of the A-chain, of which the amino, carboxyl and/or hydroxyl groups are optionally protected, and in which the cysteine groups in the 6- and 11-position are protected by a protective group $R_1$ of the aralkyl type and the cysteine group in the 7-position is protected by an acylaminomethyl group $R_2$, and that in this sequence the protective groups $R_1$ are split off by means of iodine in a polyhalogenated hydroxy or oxo compound, with formation of the disulphide bridge and thereafter, optionally after lengthening the A-chain at the amino end and/or carboxyl end, the product is condensed with a sequence which contains the disulphide bridge of the cystine of the A-chain in the 20-position and of the B-chain in the 19-position, with a cysteine group, which may be present in this sequence in the 7 position of the B-chain, being protected by an acylaminomethyl group $R_2$, thereafter the A-chain and B-chain are completed, if necessary, with the cysteine group in the 7-position of the B-chain being protected by an acylaminomethyl group $R_2$, the amino, carboxyl and/or hydroxyl protective groups are removed and, before or after this removal, the disulphide bridge is formed between the two cysteine[7] radicals of the A- and B-chain by splitting off the acylaminomethyl groups $R_2$, optionally with simultaneous oxidation to the disulphide bridge.

The sequence of formation of the various disulphide bonds indicated here is particularly advantageous. However, the sequence can also be modified. Thus, for example, it is possible to synthesise a peptide which contains the A- and B-chains of insulin linked to the disulphide bridge $A_{20} \rightarrow B_{19}$. Herein, the cysteine radicals A (7) and B (7) can be protected by the protective group $R_1$ and the cysteine radicals A (6) and A (11) by the acylamino group $R_2$. Thereafter, following the indicated method, the disulphide bridge $A_7 \rightarrow B_7$ is first formed and at the end of the synthesis the disulphide ring $A_6 \rightarrow A_{11}$ is formed.

The invention is illustrated in the examples which follow. The following abbreviations are used:
Boc = tert.-butoxycarbonyl
Acm = acetylaminomethyl
Trt = trityl
Z = carbobenzoxy
But = tert.-butyl
Me = methyl
Bpoc = 2-(p-biphenylyl)-2-propoxycarbonyl
ONp = p-nitrophenyl ester
OSu = N-hydroxysuccinimide ester
DMF = dimethylformamide.

The following systems are used in thin layer chromatography:
System 3: ethyl acetate-pyridine-water (65:20:15)
System 43A : tert.-amyl alcohol-isopropanol-water (67:26:7)
System 43C : tert.-amyl alcohol-isopropanol-water (51:21:28)
System 43E : tert.-amyl alcohol-isopropanol-water (32:32:36)
System 45 : sec.-butanol-3% strength aqueous ammonia (70:30)
System 52 : n-butanol-glacial acetic acid-water (75:7.5:21)
System 52A : n-butanol-glacial acetic acid-water (67:10:23)
System 70 : ethyl acetate-pyridine-water (40:20:40), upper phase
System 87 : isopropanol-formic acid-water (77:4:19)
System 100 : ethyl acetate-pyridine-glacial acetic acidwater (62:21:6:11)
System 101 : n-butanol-pyridine-glacial acetic acid-water (38:24:8:30)
System 101A: n-butanol-pyridine-glacial acetic acid-water (42:24:4:30)
System 102A: ethyl acetate-methyl ethyl ketone-formic acidwater (50:30:10:10)
System 107 : ethyl acetate-pyridine-water (49:24:27)
System 110 : ethyl acetate-n-butanol-pyridine-glacial acetic acid-water (42:21:21:6:10)
System 112A : n-butanol-pyridine-formic acid-water (42:24:4:20)
System 115 : ethyl acetate-pyridine-formic acid-water (63:21:10:6)

EXAMPLE 1:

H-Cys-Cys(Acm)-Thr(But)-Ser(But)-Ile-Cys-Ser(But)-Leu-OH 0.47 g of H-Cys(Trt)-Cys(Acm)-Thr(But)-Ser(But)-Ile-Cys(Trt)-Ser(But)-Leu-OH in 15 ml of trifluoroethanol are added over the course of 10 minutes to a vigorously stirred mixture of 18 ml of methylene chloride, saturated with iodine, and 180 ml of trifluoroethanol. 2 minutes after completion of the addition, a solution of 3.2 g of ascorbic acid in 60 ml of water and 30 ml of 1 M ammonium acetate are added, the solution is brought to pH 5.6 with dilute ammonia and the trifluoroethanol is very largely removed under reduced pressure. The mixture is then taken up in 100 ml of chloroform-methanol (95:5) and the organic phase is twice washed with water. After drying over sodium sulphate, the mixture is evaporated and the product shown in the title is purified by gel filtration on Sephadex-LH 20 (column: 2 × 100 cm). Eluant: chloroform-methanol (1:1).

In a thin layer chromatogram on silica gel, $Rf_{100} = 0.32$; $Rf_{52} = 0.35$.

The starting peptide can be prepared as follows:

1. Trt-Cys(Trt)-Cys(Acm)-OMe 7.0 g of Trt-Cys(Trt)-OSu and 2.0 g of H-Cys(Acm)-OMe in 50 ml of chloroform are left to stand for 20 hours at room temperature. The solution is then diluted with 100 ml of chloroform and washed with 1 N citric acid, 1 N sodium bicarbonate and water, dried over sodium sulphate and evaporated. The residue is recrystallised from ethyl acetate-ether. Melting point 197°–198°C.

2. Trt-Cys(Trt)-Cys(Acm)-OH 5.63 g of Trt-Cys(Trt)-Cys(Acm)-OMe are dissolved in 75 ml of dioxane and 17.5 ml of water and 3.71 ml of 2 N sodium hydroxide solution are cautiously added thereto. After 1 hour at 20°C, the mixture is cooled to 0°C, 3.71 ml of 2 N hydrochloric acid are added and the solution is concentrated under reduced pressure, at room temperature, to approx. 30 ml and is then diluted with 200 ml of chloroform. The solution is washed three times with water and is dried over sodium sulphate. On evaporating off the solvent, the product, which is pure according to thin layer chromatography, is obtained as a white foam.

In a thin layer chromatogram on silica gel $Rf_{45} = 0.45$; $Rf_{100} = 0.65$.

3. Z-Thr(But)-Ser(But)-OMe 16.25 g of Z-Thr(But)-OSu and 8.47 g of H-Ser(But)-OMe. HCl are added to 200 ml of ethyl acetate, 5.6 ml of triethylamine are added at 0°C and the solution is stirred for 15 hours at 20°C and washed with 1 N citric acid, 1 N sodium bicarbonate and water. After drying over sodium sulphate, the solution is evaporated, whereupon the product, which is pure according to thin layer chromatography, is obtained as an oil.

In a thin layer chromatogram on silica gel, Rf = 0.60 in chloroform-methanol (95:5) and Rf = 0.75 in toluene-acetone (1:1).

4. H-Thr(But)-Ser(But)-OMe 3.27 g of Z-Thr(But)-Ser(But)-OMe in 50 ml of ethyl acetate are hydrogenated in the presence of 0.5 g of palladium on charcoal (10% strength). After the absorption of hydrogen has ceased (1 hour), the catalyst is filtered off and the solution is evaporated. The product, which is obtained as an oil, is a single substance according to thin layer chromatography.

In a thin layer chromatogram on silica gel, Rf = 0.30 in chloroform-methanol (95:5).

5. Trt-Cys(Trt)-Cys(Acm)-Thr(But)-Ser(But)-OMe 5.43 g of Trt-Cys(Trt)-Cys(Acm)-OH and 2.33 g of H-Thr(But)-Ser(But)-OMe are dissolved in 70 ml of ethyl acetate and 1.55 g of dicyclohexylcarbodiimide and 1.02 g of N-hydroxybenzotriazole are added at 0°C. After 4 hours at 0°C and 17 hours at 4°C, the mixture is filtered and the solution is diluted with 200 ml of ethyl acetate and washed with 1 N citric acid, 1 N sodium bicarbonate and water. After drying over sodium sulphate, the solution is evaporated and the residue is reprecipitated from ether acetatepetroleum ether.

In a thin layer chromatogram on silica gel, Rf = 0.60 in toluene-acetone (1:1) and Rf = 0.45 in ethyl acetate.

6. Trt-Cys(Trt)-Cys(Acm)-Thr(But)-Ser(But)-NHNH₂

2.2 ml of hydrazine hydrate are added to 4.7 g of Trt-Cys(Trt)-Cys(Asm)-Thr(But)-Ser(But)-OMe in 11 ml of methanol and the mixture is then left to stand for 6½ hours at room temperature. The hydrazide is precipitated with 50 ml of ice-cold water, filtered off and well washed with water. The dried crude product is dissolved in 80 ml of hot toluene, the solution is concentrated somewhat and 80 ml of hexane are added at 60°C. The mixture is slowly cooled to 0°C and the product which precipitates is filtered off and washed with 1:2 toluene-hexane and with hexane. Yield 4.06 g.

In a thin layer chromatogram on silica gel, Rf = 0.26 in chloroform-methanol.

7. Z-Ser(But)-Leu-OMe 2.75 ml of triethylamine and 2.63 ml of chloroformic acid isobutyl ester are added to 5.9 g of Z-Ser(But)-OH in 20 ml of ethyl acetate at −10°C. After 10 minutes, 4.0 g of H-Leu-OMe-HCl and 3.05 ml of triethylamine are added. After stirring for 1½ hours in an ice bath, the mixture is extracted by shaking with phosphoric acid and sodium bicarbonate solution and after drying over sodium sulphate the ethyl acetate is evaporated completely. 8.2 g of a waxy mass are obtained. Melting point (after crystallisation from hexane): 56°–58°C.

In a thin layer chromatogram on silica gel, RF = 0.58 in ethyl acetate.

8 Trt-Cys(Trt)-Ser(But)-Leu-Ome 8.5 g of the above dipeptide are dissolved in 130 ml of ethyl acetate, the solution is cooled to 0°C, 19.4 ml of 1 N hydrochloric acid and 0.6 g of 10% strength palladium on charcoal are added, and a hydrogenation is carried out. After filtering off the catalyst, the ethyl acetate is evaporated, the residue is taken up in 60 ml of methylene chloride and 14.7 g of Trt-Cys(Trt)-OSu and 2.2 ml of N-methylmorpholine are added. After 48 hours at room temperature, the mixture is diluted with ethyl acetate and extracted by shaking with cold, dilute phosphoric acid and sodium bicarbonate solution. The residue obtained after drying, and evaporating the solvent, is purified in the system methanol-hexane-water (20:20:1) by a Craig distribution through 600 stages, k = 0.33. 10.1 g of a colourless foam are obtained.

In a thin layer chromatogram on silica gel, Rf = 0.46 in ethyl acetate-hexane (1:1).

9. Bpoc-Ile-Cys(Trt)-Ser(But)-Leu-OMe 1.72 g of the above protected tripeptide are dissolved in 17.2 ml of glacial acetic acid at room temperature, 4.2 ml of water are added and the mixture is stirred for 30 minutes. After adding 5 ml of glacial acetic acid, the mixture is freeze-dried, the residue is suspended in 35 ml of 70% strength tert.-butanol, a further 5 ml of water are added, the triphenylcarbinol is filtered off and the filtrate is again freeze-dried. 1.3 g of a white powder, Rf 0.30 in ethyl acetate are obtained, and are added to the mixed anhydride prepared as follows: 830 mg of Bpoc-Ile-OH in 4 ml of dimethylformamide are mixed at −15°C with 0.25 ml of N-methylmorpholine and 0.295 ml of chloroformic acid isobutyl ester. After 10 minutes, the tripeptide obtained above is added, followed by 0.166 ml of N-methylmorpholine and 4 ml of dimethylformamide. The mixture is left to stand overnight at 0°C and the product is precipitated by dropwise addition of the mixture to ice-cold aqueous potassium bicarbonate solution and is filtered off, washed well with water and dried at 40°C. The resulting product (1.98 g) is sufficiently pure for further use but can also be recrystallised from methanol-water. Melting point: 175°–177°C.

In a thin layer chromatogram on silica gel, Rf = 0.55 in ethyl acetate-hexane (8:2).

10. Trt-Cys(Trt)-Cys(Acm)-Thr(But)-Ser(But)-Ile-Cys(Trt)-Ser(But)-Leu-OMe 5.1 g of Bpoc-Ile-Cys(Trt)-Ser(But)-Leu-OMe in 44 ml of glacial acetic acid and 11 ml of water are left for 18 hours at room temperature. After adding 20 ml of glacial acetic acid, the mixture is lyophilised and is then additionally freeze-dried twice from tert.-butanol. The tacky material is triturated with 10 ml of ether, filtered off after addition of 70 ml of hexane, and washed with ether-hexane, 1:9. Yield 2.92 g.

In a thin layer chromatogram on silica gel, Rf = 0.16 in ethyl acetate.

To 3.96 g of Trt-Cys(Trt)-Cys(Acm)-Thr(But)-Ser(But)-NHNH₂ and 15 ml of dimethylformamide are added 3.3 ml of 3.3 N hydrochloric acid in dioxane at −30°C, and 0.56 ml of tert.-butyl nitrate at −15°C. After 15 minutes at −20°C the above tetrapeptide and 2.4 ml of N-methylmorpholine are added and the mixture is left overnight at 0°C. The crude product is precipitated with ice-cold water, dried and chromatographed on 290 g of silica gel, using ethyl acetatehexane, 8:2. The fractions which are pure according to thin layer chromatography are combined and evaporated to dryness, and 4.6 g of a white powder are obtained.

In a thin layer chromatogram on silica gel, Rf = 0.38 in ethyl acetate.

11.
Trt-Cys(Trt)-Cys(Acm)-Thr(But)-Ser(But)-Ile-Cys(Trt)-Ser(But)-Leu-OH 3.6 g of Trt-Cys(Trt)-Cys(Acm)-Thr(But)-Ser(But)-Ile-Cys(Trt)-Ser(But)-Leu-OMe are dissolved in 50 ml of dioxane and 17 ml of water and 4 ml of 1 N sodium hydroxide solution are added. After 1 hour at 20°C the mixture is cooled to 0°C and 4 ml of 1 N hydrochloric acid are added dropwise. The dioxane is then largely evaporated off at 20°C under reduced pressure, 20 ml of water are added and the precipitate is filtered off and dried over potassium hydroxide.

In a thin layer chromatogram on silica gel, $Rf_{45} = 0.55$ and $Rf_3 = 0.60$.

12.
H-Cys(Trt)-Cys(Acm)-Thr(But)-Ser(But)-Ile-Cys(trt)-Ser(But)-Leu-OH.2 HCl 6.94 g of Trt-Cys(Trt)-Cys(Acm)-Thr(But)-Ser(But)-Ile-Cys(Trt)-Ser(But)-Leu-OH are dissolved in 72 ml of trifluoroethanol, 8 ml of water are added and the pH is adjusted to 4.0 with 1.2 N hydrochloric acid in 90% strength trifluoroethanol and is maintained at this acidity by means of a pH-stat. After 50 minutes, 50 ml of tert.-butanol are added, the trifluoroethanol is evaporated off under reduced pressure and the solution is lyophilised. $Rf_3 = 0.40$.

EXAMPLE 2

H-Cys-Cys-Thr(But)-Ser(But)-Ile-Cys-Ser(But)-Leu-OMe

Boc-Ala-Cys-OMe

H-Cys-Cys(Acm)-Thr(But)-Ser(But)-Ile-Cys-Ser(But)-Leu-OH, obtained in Example 1, is dissolved in methanol which contains an equivalent amount of hydrogen chloride, and converted into the methyl ester by means of a solution of diazomethane in ether. In a thin layer chromatogram on silica gel in the system chloroform-methanol (85:15), this methyl ester has Rf = 0.32.

55 mg of the octapeptide methyl ester hydrochloride obtained and 19 mg of Boc-Ala-Cys(Acm)-OMe are dissolved in 8.5 ml of methanol and 1.5 ml of 0.5 M iodine solution in methanol is added. After 10 minutes at room temperature, the mixture is added dropwise to 30 ml of a 1% strength aqueous ascorbic acid solution which contains 260 mg of ammonium acetate. Hereupon the product shown in the title precipitates, together with a small amount of the two symmetrical disulphides I and II,

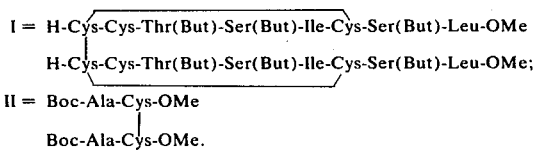

The precipitate is centrifuged off, washed with water and chromatographed on thick layer silica gel plates in chloroform-methanol (85:15). The product shown in the title, with Rf = 0.55 in the system mentioned, is isolated. The symmetrical peptide I has Rf = 0.41 and the symmetrical peptide II has Rf = 0.64.

EXAMPLE 3

Synthesis of human insulin of the formula

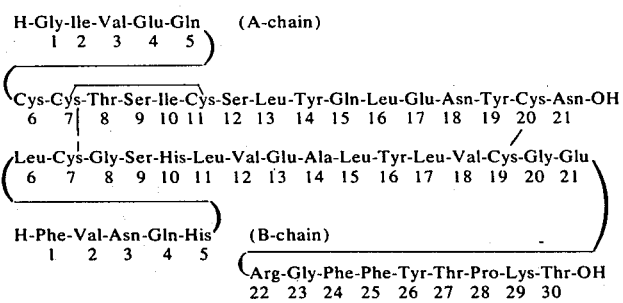

The above product is prepared using the fragment of the aminoacids 6–13 of the A-chain obtained in Example 1, namely H-Cys-Cys(Acm)-Thr(But)-Ser(But)-Ile-Cys-Ser(But)-Leu-OH (I), and the following further fragments:
II = Boc-Gly-Ile-Val-Glu(OBut)-Gln-NH-NH₂ (A-chain 1–5)
III = Boc-Phe-Val-Asn-Gln-His-Leu-Cys(Acm)-Gly-Ser(But)-His-Leu-Val-Glu(OBut)-Ala-Leu-Tyr(But)-OH (B-chain 1–16)
IV = Bpoc-Tyr(But)-Gln-Leu-Glu(OBUT)-Asn-Tyr(But)-Cys-Asn-OBut

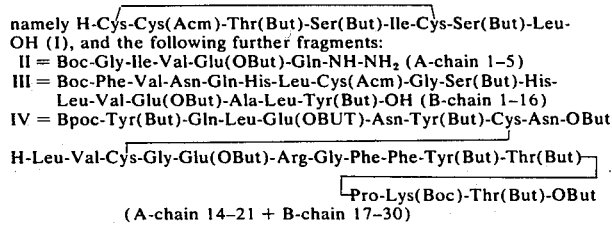

(A-chain 14–21 + B-chain 17–30)

Fragment IV is described in U.S. Pat. No. 3,862,113, issued Jan. 21, 1975. (German Offenlegungsschrift No. 2,346,147).

Fragment II can be prepared as follows:

1. Boc-Gly-Ile-Val-Glu(OBut)-Gln-OCH₃

15 ml of 3 N HCl in dioxane and 2.24 ml of tert.-butyl nitrite are added to a suspension of 8.80 g of Boc-Gly-Ile-Val-Glu(OBut)-NH-NH₂ (compare Zahn et al., Z. Naturf. 21b, 763 (1966) in 60 ml of absolute DMF at −35°C. After stirring for 15 minutes at −20°C, 2.95 g of H-Gln-OCH₃.HCl and 10 ml of N-methylmorpholine are successively added to the clear solution. The reaction mixture is stirred in an ice bath for 28 hours. The product is precipitated out with 450 ml of cold water and the precipitate is washed and dried. After repeatedly triturating it with methanol-ethyl acetate (1:20), 8.60 g of a colourless powder are left. Melting point 223°–226°C (decomposition). $[\alpha]_D^{20} = -13° \pm 1°$ (c = 1 in DMF).

In a thin layer chromatogram on silica gel, $Rf_{52} = 0.70$, Rf in the system chloroform-methanol-trifluoroethanol (7:2:1) = 0.65 and Rf in the system methyl ethyl ketone-pyridine-water (65:5:20) = 0.65

2. Boc-Gly-Ile-Val-Glu(OBut)-Gln-NH-NH$_2$ 7.15 g of Boc-Gly-Ile-Val-Glu(OBut)-Gln-OCH$_3$ are dissolved in 100 ml of methanol-DMF (1:7) and 10 ml hydrazine hydrate are added. After standing for 22 hours at room temperature, the solid mass is diluted with 70 ml of methanol and the mixture is stirred in an ice bath and filtered. The precipitate is triturated with methanol. 6.2 g of a colourless powder are obtained. This melts, with decomposition at 243°–270°C. $[\alpha]_D^{20} = -37° + 1°$ (c = 0.75 in trifluoroethanol). In a thin layer chromatogram on silica gel, $Rf_{52} = 0.40$; Rf in the system chloroform-methanol-trifluoroethanol (7:2:1) = 0.23; Rf in the system methyl ethyl ketone-pyridine-water (65:5:20) = 0.57.

Fragments I and II can be condensed as follows to give fragment V (A-chain 1–13)

3.

Boc-Gly-Ile-Val-Glu(OBUT)-Gln-Cys-Cys(Acm)-Thr(But)-Ser(But)-Ile-Cys-Ser(But)-Leu-OH (V)

5.59 ml of 2.5 N hydrogen chloride in ethyl acetate and 0.7 ml of tert.-butyl nitrite are added to 3.33 g of Boc-Gly-Ile-Val-Glu(OBut)-Gln-NH-NH$_2$ in 40 ml of DMF at −15°C. After 10 minutes at this temperature, a solution of 2.48 g of H-Cys-Cys(Acm)-Thr(But)-Ser(But)-Ile-Cys-Ser(But)-Leu-OH and 2.64 ml of N-ethylmorpholine in 12 ml of DMF are added dropwise. The mixture is left to stand for 1 hour at −10°C and 15 hours at 0°C, the reaction solution is then concentrated to a small volume and the product is precipitated with ether. The resulting crude product is subjected to a counter-current distribution. System: methanol-0.075 M ammonium acetate (pH 4.75)-chloroform-carbon tetrachloride (10:3:8:4). After 740 distribution steps, the substance is to be found in tubes 50–83. K = 0.1.

In a thin layer chromatogram on silica gel, $Rf_3 = 0.35$, $Rf_{52} = 0.70$.

Fragment III can be prepared as follows:

4. Boc-Cys(Acm)-Gly-OMe 20.5 g of Boc-Cys(Acm)-OH and 7.5 g of H-Gly-OCH$_3$ (the latter freshly liberated from the hydrochloride) are dissolved in 250 ml of chloroform, 4.7 g of N-hydroxybenzotriazole and 17.3 g of dicyclohexylcarbodiimide are added and the mixture is stirred for 4 hours at 25°C. After filtering off the dicyclohexylurea, the filtrate is diluted with a further 200 ml of chloroform and the mixture is successively washed with a little 1 N citric acid, 1 M NaHCO$_3$ and sodium chloride solution, dried over Na$_2$SO$_4$ and evaporated to dryness. The oily residue is purified by chromatography on a column containing 300 g of silica gel and filled up with ethyl acetate-petroleum ether (2:1). The pure product is eluted with ethyl acetate; it is an oil, which can be crystallised from ethyl acetate-petroleum ether; melting point 83°–86°C.

Thin layer chromatogram on silica gel: $Rf_{43A} = 0.49$; Rf in the system chloroform-methanol (9:1) = 0.42.

5. H-Cys(Acm)-Gly-OMe.HCl 5 g of Boc-Cys(Acm)-Gly-OMe are dissolved in 20 ml of methanol and 50 ml of 4.4 N HCl in dioxane are added. After 10 minutes at 25°C, the mixture is concentrated to half its volume and 100 ml of ether are added. The mother liquor is separated from the resulting amorphous precipitate and the latter is dried.

In a thin layer chromatogram on silica gel, Rf in chloroform-methanol (7:3) = 0.45; $Rf_{52} = 0.21$.

6. Boc-Leu-Cys(Acm)-Gly-OMe 32.45 g of H-Cys(Acm)-Gly-OMe.HCl and 12.5 ml of N-methylmorpholine are dissolved in 130 ml of DMF, this solution is cooled to 0°C and 46 g of Bos-Leu-ONp are added. The mixture is stirred for 1 hour at 0°C and then for 2 hours at 25°C, a further 11.8 ml of N-methylmorpholine are added and the whole is left to stand overnight at 25°C. It is then cooled to 0°C, the N-methylmorpholine hydrochloride which has crystallised out is filtered off and the filtrate is concentrated in a high vacuum. The oily residue is dissolved in 300 ml of ethyl acetate and the solution is successively washed with KOH solution (5.4 g of KOH in 100 ml of H$_2$O), 0.5 N Na$_2$CO$_3$, 1 N citric acid and water saturated with NaCl and is concentrated to dryness. The crude product is purified by trituration with ether and by reprecipitation from benzene-petroleum ether, giving an amorphous powder of melting point 112°–113°C.

In a thin layer chromatogram on silica gel, $Rf_{52} = 0.62$; $Rf_{100} = 0.90$; Rf in chloroform-methanol (8:2) = 0.65.

7. H-Leu-Cys(Acm)-Gly-OME.HCl 30 g of the product obtained under 6. are dissolved in 120 ml of methanol, 300 ml of 4.1 N HCl in dioxane are added and the mixture is left to stand for 20 minutes at 25°C. It is then concentrated to half its volume, 600 ml of ether are added, the initially smeary precipitate is converted to a powder, filtered off and washed with ether, and the residue is dried in a high vacuum over KOH. According to titration with 0.1 N NaOH, the product contains 1.1–1.3 equivalents of HCl, depending on the drying conditions.

On silica gel, $Rf_{52} = 0.20$; $Rf_{100} = 0.23$; Rf in chloroform-methanol (8:2) = 0.31.

8. Boc-Gln-His-NH-NH$_2$ 27.9 g of Boc-Gln-His-OCH$_3$ (Marchiori et al., J. Chem. Soc (C) 1967, 81) are dissolved in 280 ml of highest purity methanol, 28 ml of hydrazine hydrate are added and the mixture is left to stand for 20 hours at 25°C. It is concentrated to dryness in a high vacuum and the residue is recrystallised from methanol-ethyl acetate-petroleum ether. Melting point 187°–189°C.

In a thin layer chromatogram on silica gel, $Rf_{52} = 0.12$; $Rf_{100} = 0.1$.

9. Boc-Gln-His-Leu-Cys(Acm)-Gly-Ome 25.3 g of the product which has been obtained according to 8. and been finely powdered are suspended in 260 ml of DMF and 40 ml of 3.2 N HCl in dioxane, followed by 9.45 ml of tert.-butyl nitrite, are added at −20°C. The mixture is stirred for 15 minutes at −12°C and a solution, precooled to 0°C, of 28.6 g of the product obtained under 7., in 120 ml of DMF and 28 ml of N-methylmorpholine, is then added. After stirring for one hour at 0°C, a further 10.5 ml of N-methylmorpholine are added and the whole is then left to stand for 20 hours at 0°C. The methylmorpholine hydrochloride which was crystallised out is filtered off, the filtrate is concentrated in a high vacuum, the product is twice triturated with ethyl acetate and the powdery residue is dried. It is purified by counter-current distribution through 200 stages in the system methanol-buffer-chloroform (2:1:4) (buffer: 38.5 g of ammonium acetate + 57.2 ml of glacial acetic acid + 1,000 ml of water). The chromatographically pure pentapeptide derivative is obtained from tubes 54–88 ($r_{max} = 71$; K = 0.55) by concentration to dryness, and subliming off the buffer salt in a high vacuum at 45°C. The pentapeptide derivative is again dissolved in water at 5% strength and is lyophilised; the acetate of the product is thus obtained.

In a thin layer chromatogram on silica gel, $Rf_{43C} = 0.4$; $Rf_{110} = 0.5$; $Rf_{101A} = 0.73$.

10. H-Gln-His-Leu-Cys(Acm)-Gly-OMe.2 HCl 28 g of the product obtained under 9. are dissolved in 140 ml of trifluoroethanol and 140 ml of methanol, the solution is cooled to 0°C and 280 ml of 4.4 N HCl in dioxane are added. The mixture is allowed to react for 5 minutes at 25°C and is again cooled to 0°C, precipitation is effected by addition of 560 ml of ethyl acetate and 280 ml of petroleum ether and the supernatant solution is decanted. The amorphous residue is converted to a powder by trituration with ethyl acetate-petroleum ether (2:1) and is dried in a high vacuum at room temperature over KOH.

On silica gel, $Rf_{101A} = 0.4$; $Rf_{107} = 0.35$.

11. Boc-Asn-Gln-His-Leu-Cys(Acm)-Gly-OMe 27.3 g of the product obtained under 10 and 40.5 g of Boc-Asn-ONp are dissolved in 140 ml of DMF, 12.6 ml of N-methylmorpholine are added, the mixture is stirred for 1 hour at 25°C, a further 8.4 ml of N-methylmorpholine are added and the whole is left to stand overnight. After cooling to 0°C, the methylmorpholine hydrochloride is filtered off and the crude product is precipitated from the filtrate by means of ethyl acetate and is purified by reprecipitation from methanol-ether.

The hexapeptide derivative is obtained as an amorphous powder of melting point 175°–77°C (decomposition).

On silica gel, $Rf_{101A} = 0.6$; $Rf_{107} = 0.65$; $Rf_{43C} = 0.3$; $Rf_{110} = 0.45$.

12. H-Asn-Gln-His-Leu-Cys(Acm)-Gly-OMe.2 HCl 26 g of the product obtained under 11. are dissolved in 130 ml of trifluoroethanol and 130 ml of methanol, 260 ml of 4.8 N HCl in dioxane are added and the mixture is left to stand for 20 minutes at 25°C. The hexapeptide derivative is then precipitated in the form of a powder by allowing 520 ml of ethyl acetate and 260 ml of petroleum ether to run into the mixture at 0°C, and is filtered off and dried in a high vacuum over KOH. On silica gel: $Rf_{101A} = 0.3$; $Rf_{43C} = 0.12$.

13. Boc-Val-Asn-Gln-His-Leu-Cys(Acm)-Gly-OMe 33 g of Boc-Val-ONp, 27 g of the product obtained under 12. and 18 ml of N-methylmorpholine are dissolved in 400 ml of DMF and the solution is warmed to 50°C for 6½ hours. It is then evaporated in a high vacuum until an oil is obtained and the crude product is precipitated by addition of ether. It is purified by reprecipitation from methanol–5% strength NaHCO$_3$ solution and from methanol-ethyl acetate, melting point 210°–12°C. On silica gel: $Rf_{101A} = 0.6$; $Rf_{52} = 0.15$; $Rf_{43C} = 0.35$.

14. Boc-Val-Asn-Gln-His-Leu-Cys(Acm)-Gly-OH 20.6 g of the product obtained under 13 are dissolved in 164 ml of methanol and 226 ml of water whilst heating to the boil, the solution is cooled to 10°C, 82 ml of 1 N NaOH are added and the whole is then left to stand for 8 hours at 25°C. It is neutralised by addition of 82 ml of 1 N HCl and concentrated to a volume of approx. 250 ml, and this solution is purified by subjecting it to a counter-current distribution in the system n-butanol-ammonium acetate buffer (7.7 g of ammonium acetate + 5.72 ml of glacial acetic acid + 1,000 ml of water; pH-4.75). After 166 stages, the pure heptapeptide derivative is isolated, as an amorphous powder of melting point 220°C (decomposition), from tubes No. 54–75 ($r_{max} = 64$; K = 0.63) by evaporating the contents to dryness, subliming off the buffer and drying the residue in a high vacuum at 45°C. On silica gel: $Rf_{43E} = 0.45$; $Rf_{101} = 0.5$; $Rf_{87} = 0.55$.

15. H-Val-Asn-Gln-His-Leu-Cys(Acm)-Gly-OH.2 HCl 9 g of the product obtained under 14. are suspended in 225 ml of 0.72 N HCl in 94% strength glacial acetic acid and the mixture is stirred for 30 minutes at 25°C, a clear solution being obtained after approx. 20 minutes. This solution is lyophilised and the dry residue is post-dried in a high vacuum at 30°C.

On silica gel: $Rf_{43E} = 0.18$; $Rf_{45} = 0.18$; $Rf_{101A} = 0.3$.

16. Boc-Phe-Val-Asn-Gln-His-Leu-Cys(Acm)-Gly-OH 467 mg of the product obtained under 15. are dissolved in 10 ml of DMF and 0.5 ml of water, 765 mg of (Boc-Phe)$_2$O and 275 $\mu$l of N-methylmorpholine are added and the mixture is left to stand for 3 hours at 50°C. It is then concentrated in a high vacuum until a jelly-like residue forms, which is triturated with 0.1 M ammonium acetate buffer (pH 4.75), filtered off, washed with water and dried. The crude product is purified by trituration with ether and subsequently by reprecipitation from trifluoroethanol-ether. On silica gel: $Rf_{43E} = 0.45$; $Rf_{45} = 0.27$; $Rf_{52} = 0.21$.

17. Boc-Phe-Val-Asn-Gln-His-Leu-Cys(Acm)-Gly-Ser(But)-His-Leu-Val-Glu(OBut)-Ala-Leu-Tyr(But)-OMe 1.66 g of the product obtained under 16. and 290 mg of toluenesulphonic acid monohydrate are dissolved in 32 ml of absolute DMF whilst warming to 45°C and a solution of 1.7 g of H-Ser(But)-His-Leu-Val-Glu(OBut)-Ala-Leu-Tyr(But)-OMe (compare Zahn et al., Ann. Chem. 731, 91 (1970)) in 18 ml of DMF and a solution of 467 mg of N-hydroxybenzotriazole in 6 ml of DMF are added successively; finally, 2.51 g of dicyclohexylcarbodiimide in the solid form are also added, and the whole is stirred for 40 minutes at 45°C. The mass, which solidifies to a jelly, is homogenised with 300 ml of ether and the finely flocculent precipitate which forms is filtered off, washed with ether and dried. For purification, the crude product, in 80 ml of trifluoroethanolglacial acetic acid (19:1 parts by volume), is warmed to 50°C for 40 minutes, and the product is precipitated by adding 250 ml of ether, filtered off and dried in a high vacuum over KOH. It is an amorphous powder of decomposition point approx. 250°C, which is sparingly soluble in most solvents. According to titrations, it contains 1.15 equivalents of toluenesulphonic acid and 0.85 equivalent of acetic acid.

On silica gel: $Rf_{100} = 0.3$; $Rf_{43C} = 0.35$; $Rf_{70} = 0.6$; $Rf_{110} = 0.6$.

18.

Boc-Phe-Val-Asn-Gln-His-Leu-Cys(Acm)-Gly-Ser(-But)-His-Leu-Val-Glu(OBut)-Ala-Leu-Tyr(But)-OH (III)

6.4 g of the product obtained under 17. are dissolved in 470 ml of trifluoroethanol at 65°c, 145 ml of water and 191 ml of 1 N NaOH are added, and the mixture is stirred for 5 hours at 50°C, cooled to 20°C and neutralised with 191 ml of 1 N HCl. The crude product is precipitated by concentrating the mixture to half its volume and adding 950 ml of water. The pH is adjusted to 7.0 by adding 1 N NaOH, the mixture is left to stand overnight at 0°C and the product is filtered off, washed with water and dried. It is purified by distribution through 680 stages in the system methanol-1 N acetic acid-chloroform-carbon tetrachloride (10:3:5:4); apparatus with 200 distribution elements, and 25 ml phase volumes, circulatory process. The pure hexadecapeptide is isolated from tubes 540–594 ($r_{max}$ = 550; K = 4.2) by concentration until a gel is formed, and lyophilisation. To remove the bound acetic acid, the product is dissolved in trifluoroethanol, a 5-fold volume of water is added, the pH value is adjusted to 7.0, the mixture is left to stand overnight at −10°C and the product is filtered off, washed and dried. An amorphous, sparingly soluble powder of decomposition point approx. 230°C is obtained.

On silica gel: $Rf_{43C} = 0.3$; $Rf_{52A} = 0.3$; $Rf_{70} = 0.5$; $Rf_{110} = 0.45$.

Fragment III can be condensed as follows with fragment IV, described in German Offenlegungsschrift No. 2,346,147, to give protected A-chain 14–21 + protected B-chain 1–30 (VI):

19.
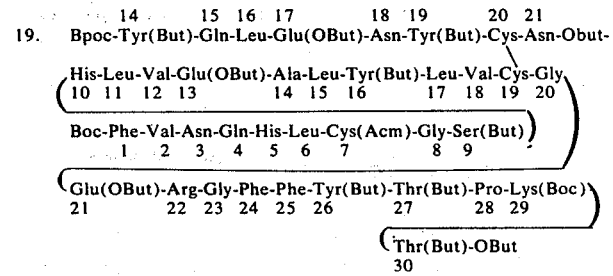

2.12 g of the product (III) described under 18. and 2.74 g of

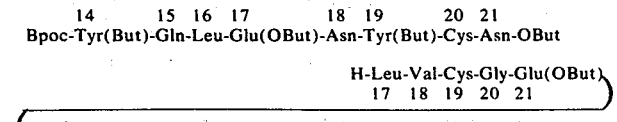

as the hydrochloride, as well as 0.94 g of N-hydroxybenzotriazole (hydrate) are dissolved in 92 ml of DMF at 45°C, 0.63 g of dicyclohexylcarbodiimide is added and the mixture is stirred for 4½ hours at 45°C. The solution is then added dropwise to 850 ml of ether and the finely flocculent precipitate is filtered off and washed with ether.

The crude product is subjected to a counter-current distribution in the system methanol-0.1 M ammonium acetate (pH 7.0)-chloroform-carbon tetrachloride (10:3:5:4). After 1,200 distribution steps, the product is to be found in tubes 15–42; K = 0.03.

In a thin layer chromatogram on silica gel, the substance shows the following Rf values: $Rf_{102A} = 0.50$; $Rf_{52A} = 0.55$; $Rf_{100} = 0.45$.

20.
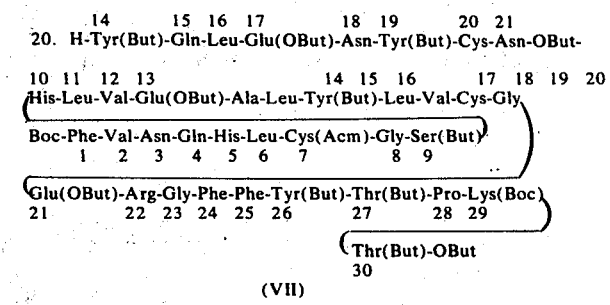

(VII)

The Bpoc group can be split off from the product (VI), described under 19, by the process of German Offenlegungsschrift No. 2,346,147, giving the above product (VII):

1.1 g of the product V described under 19 are dissolved in 150 ml of 90% strength trifluoroethanol, the solution is adjusted to pH 0.5 with 0.12 N hydrogen chloride in 90% strength trifluoroethanol and this pH value is maintained by means of a pH-stat. After 1½ hours, 1 ml of pyridine is added and the solution is evaporated to dryness. The residue is twice triturated with ether, filtered off and dried. The product (the hydrochloride of VII) has the following Rf values in a thin layer chromatogram on silica gel: $Rf_{52A} = 0.25$; $Rf_{100} = 0.30$; $Rf_{43C} = 0.40$; $Rf_{102A} = 0.35$.

Fragment VII can be condensed with fragment V, described under 3., to give the protected sequences A and B of human insulin (VIII), linked via a disulphide bridge:

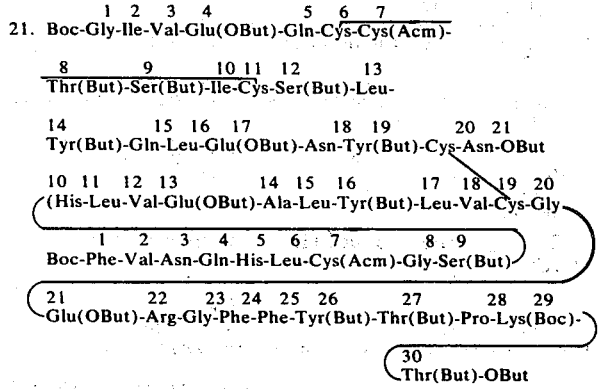

950 mg of Boc-Gly-Ile-Val-Glu(OBut)-Gln-Cys-Cys-(Acm)-Thr(But)-Ser(But)-Ile-Cys-Ser(But)-Leu-OH (V) and 360 mg of the product described under 20. are dissolved in 15 ml of DMF and 70 μl of N-ethylmorpholine, 136 mg of N-hydroxybenzotriazole and 150 ml of dicyclohexylcarbodiimide are added. The solution is kept for 5 hours at 45°C and then cooled, and 100 ml of ether are added. The precipitate is filtered off, washed with ether and dried.

The crude product is purified bby subjecting it to a counter-current distribution in the system by 0.1 M ammonium acetate (pH 4.75)-chloroform-carbon tetrachloride (20:6:11:9). After 1,425 distribution steps, the substance is present in tubes 42–66. K = 0.05. In a thin layer chromatogram on silica gel, the product has the following Rf values: $Rf_{45} = 0.35$; $Rf_{52} = 0.40$; $Rf_{115} = 0.60$.

22. Human insulin (h-insulin)

a. The protective groups of the tert.-butyl type are removed from the product described under 21. by means of trifluoroacetic acid, and the mercapto-protective groups are removed by means of iodine, whilst at the same time forming the second disulphide bridge between the chains A and B:

55 mg of the product described under 21. are treated with 95% strength trifluoroacetic acid for 30 minutes at room temperature. The solution is diluted with 60 ml of 50% strength acetic acid and immediately added to 15 ml of 0.1 M iodine solution in glacial acetic acid. After 10 minutes, the mixture is decolourised with 1.8 ml of 1 M aqueous ascorbic acid solution, and the solution thus obtained is desalinated on a 450 ml column of Sephadex G 25 in 50% strength acetic acid. The eluate, which absorbs in the UV at 280 nm, is concentrated in vacuo and freeze-dried. The h-insulin is obtained from this crude product by distribution in the system tert.-butanol-1 M ammonium acetate (pH 7.1)-chloroform (10:10:0.5); K = 0.35. The product crystallises in the typical rhombohedral crystals from an 0.095 M Na citrate buffer of pH 6.0, containing 0.03 M NaCl, 0.012 M $ZnCl_2$ and 16% by volume of acetone. In a thin layer chromatogram on cellulose, $Rf_{101} = 0.55$; $Rf_{112A} = 0.45$. Electrophoreses on cellulose acetate: pH 1.9; migration distance 9 cm towards the anode; pH 8.6: migration distance 7 cm towards the cathode (buffer according to Brandenburg et al., Hoppe-Seyler's Z. Physiol. Chem. 353, 599 (1972)).

b. The mercapto-protective groups are first removed from the product described under 21. by means of iodine, with simultaneous formation of the second disulphide bridge, and thereafter the protective groups of the tert.-butyl type are removed with trifluoroacetic acid.

55 mg of the product described under 21., in 20 ml of 87.5% strength acetic acid, are added dropwise to 15 ml of 0.1 M iodine solution in glacial acetic acid, diluted with 40 ml of 50% strength acetic acid, and the mixture is stirred for 10 minutes at room temperature. The excess iodine is decolourised with 1.8 ml of 1 M aqueous ascorbic acid solution and the reaction mixture is desalinated on a 450 ml column of Sephadex G 25 in 50% strength acetic acid. The eluate, which absorbs in the UV at 280 nm, is concentrated in vacuo and freee-dried. The residue is treated with 95% strength trifluoroacetic acid for 30 minutes and precipitated with ether. h-Insulin is obtained from this crude product in the way described under 22.

EXAMPLE 4

Formation of the cystine bond from S-trityl-cysteine-peptide chains in the presence of a S-Acm-cysteine-peptide chain 0.3 ml of an 0.2 M solution of iodine in methylene chloride is added to 2.7 mg (5 μmol) of Acetyl-Gly-Cys(Trt)-Gly-$OCH_3$ (I) and 2.7 mg (5 μmol) of Z-Phe-Cys(Acm)-Gly-$OCH_3$ (II), dissolved in 0.8 ml of 1,1,1,3,3,3-hexafluoro-2-propanol. After 10 minutes' stirring at room temperature, the mixture is decolourised with 0.4 ml of 1 M aqueous scorbic acid solution. According to a thin layer chromatogram on silica gel, the reaction solution contains, as the sole cystine-peptide,

and in addition contains unchanged Acm-cysteine-peptide (II). The RF values of compounds I, II and III in the systems chloroform-methanol (85:15, V:V) = system A, and chloroform-trifluoroethanol (85:15, V:V) = system B, migration distance 15 cm, are as follows:

|   | I | II | III |
|---|---|---|---|
| A | 0.53 | 0.58 | 0.17 |
| B | 0.24 | 0.26 | 0.00 |

The starting materials can be prepared as follows:

I. a. Trt-Cyst(Trt)-Gly-OMe 4.28 ml of triethylamine, followed by 20 g of Trt-Cys(Trt)-OSu.$C_6H_6$ (B. Kamber et al., Helv. Chim. Acta 53, 556 (1970)) are added to a suspension of 3.86 g of H-Gly-OMe. HCl in 60 ml of DMF whilst stirring at 22°C and the mixture is then stirred for 2 hours and left to stand overnight. The triethylamine hydrochloride formed is then filtered off and the dipeptide derivative is precipitated as an amorphous powder by adding the filtrate dropwise to 500 ml of water at 0°C. In a thin layer chromatogram on silica gel, Rf in the system cyclohexane-ethyl acetate (1:1) = 0.51; Rf in toluene-acetone (8:2) = 0.6.

b. H-Cys(Trt)-Gly-OMe 4 g of Trt-Cys(Trt)-Gly-OMe are dissolved in 40 ml of glacial acetic acid and a total of 10 ml of water are added dropwise over the course of 5 minutes. After completion of the dropwise addition, the mixture is stirred for a further 30 minutes at room temperature, a further 30 ml of water are added, the whole is stirred further for 30 minutes at 0°C and the triphenylcarbinol produced is then filtered off. The filtrate is covered with ethyl acetate and is adjusted to pH 9–10 with saturated sodium carbonate solution at 0°C. The organic phase is washed with water and concentrated to dryness, giving a yellow, resinous product. On silica gel, Rf in $CHCl_3$-MeOH (9:1) = 0.6; Rf in butyl acetate-MeOH (9:1) = 0.35; $Rf_{52}$ = 0.6.

c. Acetyl-Gly-Cys(Trt)-Gly-OMe 1.27 g of Acetyl-Gly-OH and 1.51 ml of triethylamine are dissolved in 11 ml of ethyl acetate and 2 ml of DMF, the solution is cooled to −20°C and 1.33 ml of pivalic acid chloride are added. The mixture is stirred for 15 minutes at −10°C, a solution of 3.62 g of H-Cys(Trt)-Gly-OMe in 15 ml of ethyl acetate and 1 ml of DMF is then added and the whole is stirred for 1 hour at 0°C and left to stand overnight at 5°C. The mixture is then diluted with ethyl acetate, washed successively with citric acid solution, sodium bicarbonate solution and water and concentrated to dryness. The residue is crystallised from ethyl acetate-petroleum ether; melting point 192°–193°C.

On silica gel: Rf in $CHCl_3$-MeOH (9:1) = 0.36; Rf in butyl acetate-MeOH (8:2) = 0.35; $Rf_{52}$ = 0.65.

II. Z-Phe-Cys(Acm)-Gly-OMe 1.95 g of Z-Phe-OH and 0.77 ml of N-methylmorpholine are dissolved in 10 ml of ethyl acetate, 0.8 ml of pivalic acid chloride is added at −20°C and the mixture is stirred for 15 minutes at −10°C. A solution of 1.5 g of H-Cys(Acm)-Gly-OMe.HCl (compare Example 3 under 5) in 5 ml of DMF and 20 ml of ethyl acetate is then added, as is 0.66 ml of N-methylmorpholine, and the mixture is stirred for 1 hour at 0°C and left to stand overnight at 5°C. It is worked up by taking up in n-butanol, washing successively with citric acid solution, sodium bicarbonate and water and concentrating the organic phase to dryness. The residue is recrystallised from methanol-ethyl acetate-petroleum ether; melting point 185°–186°C. On silica gel: Rf in $CHCl_3$-MeOH (9:1) = 0.6; $Rf_{52}$ = 0.65; $Rf_{43C}$ = 0.6.

2.7 mg of peptide I and 2.7 mg of peptide II, dissolved in 1.2 ml of 2,2,2-trifluoroethanol, are treated with 0.3 ml of 0.2 M aqueous iodine solution containing KI (Titrisol, Merck) in the same manner as described above. After 10 minutes at room temperature, the mixture is worked up as indicated. The cystine-peptide III and the cysteine-peptide II are eluted as the sole peptides by thin layer chromatography of the reaction solution. Rf values as above.

The same results are obtained if instead of trifluoroethanol the following solvents are used: 1,1,1,3,3,3-hexachloroacetone; 1,1,1,3,3,3-hexafluoroacetone trihydrate; 2,2,2-trichloroethanol; 2,2,2-tribromoethanol; 1,1,1-trifluoroacetone.

What we claim is:

1. In a process for the manufacture of peptides containing more than one disulphide bond from peptides containing cysteine radicals and in which one or two cysteine radicals which are to be linked are protected by a mercapto-protective group $R_1$, which is an aralkyl radical containing at least two cyclic residues, whose aliphatic part, which is bonded to the sulphur of the mercapto group, is lower alkyl or cycloalkyl with at most 7 carbon atoms and whose arylic part is at least one phenyl group which is unsubstituted or substituted by one or more members of the group consisting of lower alkyl, lower alkoxy and halogen, and two other cysteine radicals which are to be linked are protected by an acylaminomethyl group $R_2$, of the formula —$CH_2$—NH—COR, wherein —COR represents the acyl radical of a carboxylic acid, the improvement which comprises removing the protective group $R_1$ by reacting the peptide with iodine in the presence of polyhalogenated lower alkanol or a polyhalogenated di-lower alkyl ketone, at the same time forming the disulphide bond between the cysteine radicals which were protected by $R_1$ and forming the second disulphide bridge after removal of the polyhalogenated compound.

2. Process as claimed in claim 1, characterised in that trifluoroethanol or hexafluoro-2-propanol is used as the polyhalogenated compound.

3. Process as claimed in claim 1, characterised in that the trityl group is used as the mercapto-protective group $R_1$.

4. Process as claimed in claim 1, wherein R is lower alkyl.

5. Process as claimed in claim 1 for the manufacture of insulin characterised in that a sequence is prepared which contains at least the aminoacids 6–11 of the A-chain, of which the amino, carboxyl and/or hydroxyl groups are optionally protected, and in which the cysteine groups in the 6- and 11-position are protected by a protective group $R_1$ of the aralkyl type and the cysteine group in the 7-position is protected by an acylaminomethyl group $R_2$, and that in this sequence the protective groups $R_1$ are split off by means of iodine in a polyhalogenated lower alkanol or polyhalogenated di-lower alkyl ketone, with formation of the disulphide bridge and thereafter, optionally after lengthening the A-chain at the amino end and/or carboxyl end, the product is condensed with a sequence which contains the disulphide bridge of the cystine of the A-chain in the 20-position and of the B-chain in the 19-position, with a cysteine group, which may be present in this sequence in the 7-position of the B-chain, being protected by an acylaminomethyl group $R_2$, thereafter the A-chain and B-chain are completed, if necessary, with the cysteine group in the 7-position of the B-chain being protected by an acylaminomethyl group $R_2$, the amino, carboxyl and/or hydroxyl protective groups are removed and, before or after this removal, the disulphide bridge is formed between the two cysteine[7] radicals of the A- and B-chain by splitting off the acylaminoethyl groups $R_2$, optionally with simultaneous oxidation to the disulphide bridge.

6. Trt-Cys(Trt)-Cys(Acm)-OH and its methyl ester.

7. Trt-Cys(Trt)-Cys(Acm)-Thr(But)-Ser(But)-Ile-Cys(Trt)-Ser(But)-Leu-OH and its methyl ester.

8. H-Cys(Trt)-Cys(Acm)-Thr(But)-Ser(But)-Ile-Cys(Trt)-Ser(But)-Leu-OH.

9. H-Cys-Cys(Acm)-Thr(But)-Ser(But)-Ile-Cys-Ser(But)-Leu-OH.

10. Boc-Phe-Val-Asn-Gln-His-Leu-Cys(Acm)-Gly-Ser(But)-His-Leu-Val-Glu(OBut)-Ala-Leu-Tyr(But)-OH.

11. Boc-Gly-Ile-Val-Glu-(OBut)-Gln-Cys-Cys-(Acm)-Thr(But)-Ser(But)-Ile-Cys-Ser(But)-Leu-OH.

12. A member selected from the group consisting of

```
        14      15 16 17       18   19      20  21
H-Tyr(But)-Gln-Leu-Glu(OBut)-Asn-Tyr(But)-Cys-Asn-OBut 10 11 12  13              14  15  16        17 18 19  20
His-Leu-Val-Glu(OBut)-Ala-Leu-Tyr(But)-Leu-Val-Cys-Gly

Boc-Phe-Val-Asn-Gln-His-Leu-Cys(Acm)-Gly-Ser(But)
 1   2   3   4   5   6   7      8     9

Glu(OBut)-Arg-Gly-Phe-Phe-Tyr(But)-Thr(But)-Pro-Lys(Boc)
  21       22  23  24  25   26        27      28   29

Thr(But)-OBut and the
                                       30
        14
Bpoc-Tyr(But)-derivative thereof.
```

13.

```
 1   2   3   4       5       6   7    8
Boc-Gly-Ile-Val-Glu(OBut)-Gln-Cys-Cys(Acm)-Thr(But)-

9      10 11  12       13
Ser(But)-Ile-Cys-Ser(But)-Leu-
```

-continued

```
     14     15 16 17       18   19      20  21
Tyr(But)-Gln-Leu-Glu(OBut)-Asn-Tyr(But)-Cys-Asn-OBut 10 11 12  13              14 15 16        17 18 19 20
His-Leu-Val-Glu(OBut)-Ala-Leu-Tyr(But)-Leu-Val-Cys-Gly 1   2   3   4   5   6   7       8   9
Boc-Phe-Val-Asn-Gln-His-Leu-Cys(Acm)-Gly-Ser(But)

21        22  23  24  25  26    27       28  29
Glu(OBut)-Arg-Gly-Phe-Phe-Tyr(But)-Thr(But)-Pro-Lys(Boc)

30
                 Thr(But).
```

14.

```
 1   2   3   4   5   6   7      8   9  10 11
H-Gly-Ile-Val-Glu-Gln-Cys-Cys(Acm)-Thr-Ser-Ile-Cys 12  13  14  15  16  17  18  19  20  21
Ser-Leu-Tyr-Gln-Leu-Glu-Asn-Tyr-Cys-Asn-OH 10 11 12 13 14 15 16 17 18 19 20 21
His-Leu-Val-Glu-Ala-Leu-Tyr-Leu-Val-Cys-Gly-Glu 1   2   3   4   5   6   7      8   9
H-Phe-Val-Asn-Gln-His-Leu-Cys(Acm)-Gly-Ser 22  23  24  25  26  27  28  29  30
         Arg-Gly-Phe-Phe-Tyr-Thr-Pro-Lys-Thr-OH.
```

15.

```
 1   2   3   4       5       6   7   8        9       10 11
Boc-Gly-Ile-Val-Glu(OBut)-Gln-Cys-Cys-Thr(But)-Ser(But)-Ile-Cys- 12       13  14     15   16  17       18   19
Ser(But)-Leu-Tyr(But)-Gln-Leu-Glu(OBut)-Asn-Tyr(But)-

20  21
                             Cys-Asn-OBut 10 11 12  13              14 15  16       17
His-Leu-Val-Glu(OBut)-Ala-Leu-Tyr(But)-Leu- 18  19 20  21
                        Val-Cys-Gly-Glu(OBut)

1   2   3   4   5   6   7      8   9
Boc-Phe-Val-Asn-Gln-His-Leu-Cys-Gly-Ser(But)

22  23  24  25  26       27       28  29   30
Arg-Gly-Phe-Phe-Tyr(But)-Thr(But)-Pro-Lys(Boc)-Thr(But).
```

* * * * *

UNITED STATES PATENT AND TRADEMARK OFFICE
CERTIFICATE OF CORRECTION

PATENT NO. : 3,994,871
DATED : November 30, 1976
INVENTOR(S) : Bruno Kamber et al It is certified that error appears in the above-identified patent and that said Letters Patent are hereby corrected as shown below:

Column 11, under Example 2, insert a connecting line from "Cys" on line 55 (second occurrence) to "Cys" on line 58.

Column 12, first formula, delete the connecting line between "Cys", first line (first occurrence) and "Cys", second line (first occurrence) and insert a connecting line between "Cys", first line (second occurrence) and "Cys", second line (second occurrence).

Column 12, under Example 3, line 49, delete "(OBUT)" and insert --- (OBut) ---.

Column 18, delete line 2 of the third formula and substitute ---
10  11  12  13      14  15  16      17  18  19  20
His-Leu-Val-Glu(OBut)-Ala-Leu-Tyr(But)-Leu-Val-Cys-Gly ---.

Column 23, claim 12, in the formula, draw a connecting line between "Cys", line 1, to "Cys", line 2;   draw a connecting line between "His" on line 2 to "(But)" on line 3;   draw a connecting line between "Gly" on line 2 to "Glu" on line 4;   draw a connecting line between "(Boc)" on line 4 to "Thr" on line 5.

Column 24, claim 15, in the formula, draw a connecting line between "Cys" on line 3 to "Cys" on line 5.

Signed and Sealed this

Fifth Day of April 1977

[SEAL]

Attest:

RUTH C. MASON
*Attesting Officer*

C. MARSHALL DANN
*Commissioner of Patents and Trademarks*